(12) United States Patent
Miller et al.

(10) Patent No.: US 11,523,910 B2
(45) Date of Patent: Dec. 13, 2022

(54) RADIO-OPAQUE MARKERS IN ADDITIVELY MANUFACTURED IMPLANTS

(71) Applicant: Warsaw Orthopedic, Inc., Warsaw, IN (US)

(72) Inventors: Keith E. Miller, Germantown, TN (US); Adriaan J. Kuyler, Germantown, TN (US); Colleen M. Mignogna, Southaven, MS (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 461 days.

(21) Appl. No.: 16/535,686

(22) Filed: Aug. 8, 2019

(65) Prior Publication Data

US 2021/0038396 A1 Feb. 11, 2021

(51) Int. Cl.
| | | |
|---|---|---|
| *B29C 64/118* | (2017.01) | |
| *A61F 2/30* | (2006.01) | |
| *A61L 27/50* | (2006.01) | |
| *B33Y 80/00* | (2015.01) | |
| *B33Y 10/00* | (2015.01) | |
| *B33Y 30/00* | (2015.01) | |
| *B33Y 70/00* | (2020.01) | |

(52) U.S. Cl.
CPC .......... *A61F 2/30942* (2013.01); *A61L 27/50* (2013.01); *B29C 64/118* (2017.08); *A61F 2002/30985* (2013.01); *B33Y 10/00* (2014.12); *B33Y 30/00* (2014.12); *B33Y 70/00* (2014.12); *B33Y 80/00* (2014.12)

(58) Field of Classification Search
None
See application file for complete search history.

(56) References Cited

U.S. PATENT DOCUMENTS

| | | | | |
|---|---|---|---|---|
| 5,256,334 | A * | 10/1993 | Smid ................... | A61L 24/001 |
| | | | | 252/478 |
| 6,719,799 | B1 * | 4/2004 | Kropf .................. | A61F 2/4014 |
| | | | | 623/19.12 |
| 7,476,252 | B2 | 1/2009 | Foley | |
| 2008/0161927 | A1 | 7/2008 | Savage et al. | |
| 2008/0234687 | A1 * | 9/2008 | Schaller .................. | A61F 2/44 |
| | | | | 606/90 |
| 2009/0192591 | A1 * | 7/2009 | Ryan ..................... | A61F 2/2436 |
| | | | | 623/2.11 |

(Continued)

OTHER PUBLICATIONS

Ferng, Alice, Thoracic Vertebrae, Apr. 26, 2016 (Accessed May 3, 2022 via Internet Archive), Ken Hub, https://www.kenhub.com/en/library/anatomy/thoracic-vertebrae (Year: 2016).*

*Primary Examiner* — Matthew J Daniels
*Assistant Examiner* — Andrew L Swanson
(74) *Attorney, Agent, or Firm* — Fox Rothschild LLP; P. Marshall Ticer

(57) ABSTRACT

An approach is provided for a three-dimensional (3D) printing method for forming a 3D object. The approach provides for printing a structure of the 3D object by depositing a thermoplastic material, in which the thermoplastic material is radiolucent. The approach provides for printing one or more radio-opaque markers by depositing another material, which includes at least a radio-opaque material. The approach integrates the one or more radio-opaque markers with the structure of the 3D object.

20 Claims, 10 Drawing Sheets

(56) References Cited

U.S. PATENT DOCUMENTS

2010/0185287 A1\* 7/2010 Allard ................... A61F 2/4611
                                                        623/17.11
2017/0105844 A1\* 4/2017 Kuyler .................... A61F 2/447
2020/0179723 A1\* 6/2020 Gagneur .............. A61N 5/1075

\* cited by examiner

RADIO-OPAQUE MARKERS IN ADDITIVELY MANUFACTURED IMPLANTS

BACKGROUND

A variety of three-dimensional (3D) printing processes may be used to create 3D objects, such as implantable medical devices (hereinafter "implant"). A 3D printing process may use a continuous filament of a thermoplastic material, such as polyetheretherketone (PEEK) or polyetherketoneketone (PEKK), to print the implant. However, PEEK and PEKK are radiolucent materials, which do not appear on medical images, such as x-rays.

Typically, to distinguish the implant on medical images, radio-opaque markers are added to the implant after the implant was manufactured. For example, one or more small holes may be drilled into the manufactured implant, and bio-compatible metal pins may be inserted into each of the small holes. However, the additional holes drilled into the implant may weaken the structure of the implant. Moreover, the radio-opaque pins may not provide adequate information related to the functions, features, and/or orientation of the implant during an operation or post-operation.

SUMMARY

The present disclosure relates generally to implantable medical devices and, more particularly, to radio-opaque markers formed in the formation of respective implantable medical devices.

In one or more cases, the disclosed technology relates to a three-dimensional (3D) printing method for forming a 3D object. In one or more cases, the method includes printing a structure of the 3D object by depositing a thermoplastic material, in which the thermoplastic material is radiolucent. In one or more cases, the method includes printing one or more radio-opaque markers by depositing another material, which includes at least a radio-opaque material. In one or more cases, the one or more radio-opaque markers are integrated with the structure of the 3D object.

In one or more cases, a three-dimensional (3D) printing method for forming an implantable medical device. In one or more cases, the method includes printing a structure of the implantable medical device by depositing a thermoplastic material, in which the thermoplastic material is radiolucent. In one or more cases, the method includes printing one or more radio-opaque markers by depositing another material, in which the other material includes at least a radio-opaque material. In one or more cases, the one or more radio-opaque markers are integrated with the structure of the implantable medical device during the 3D printing method.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

Figure 1:
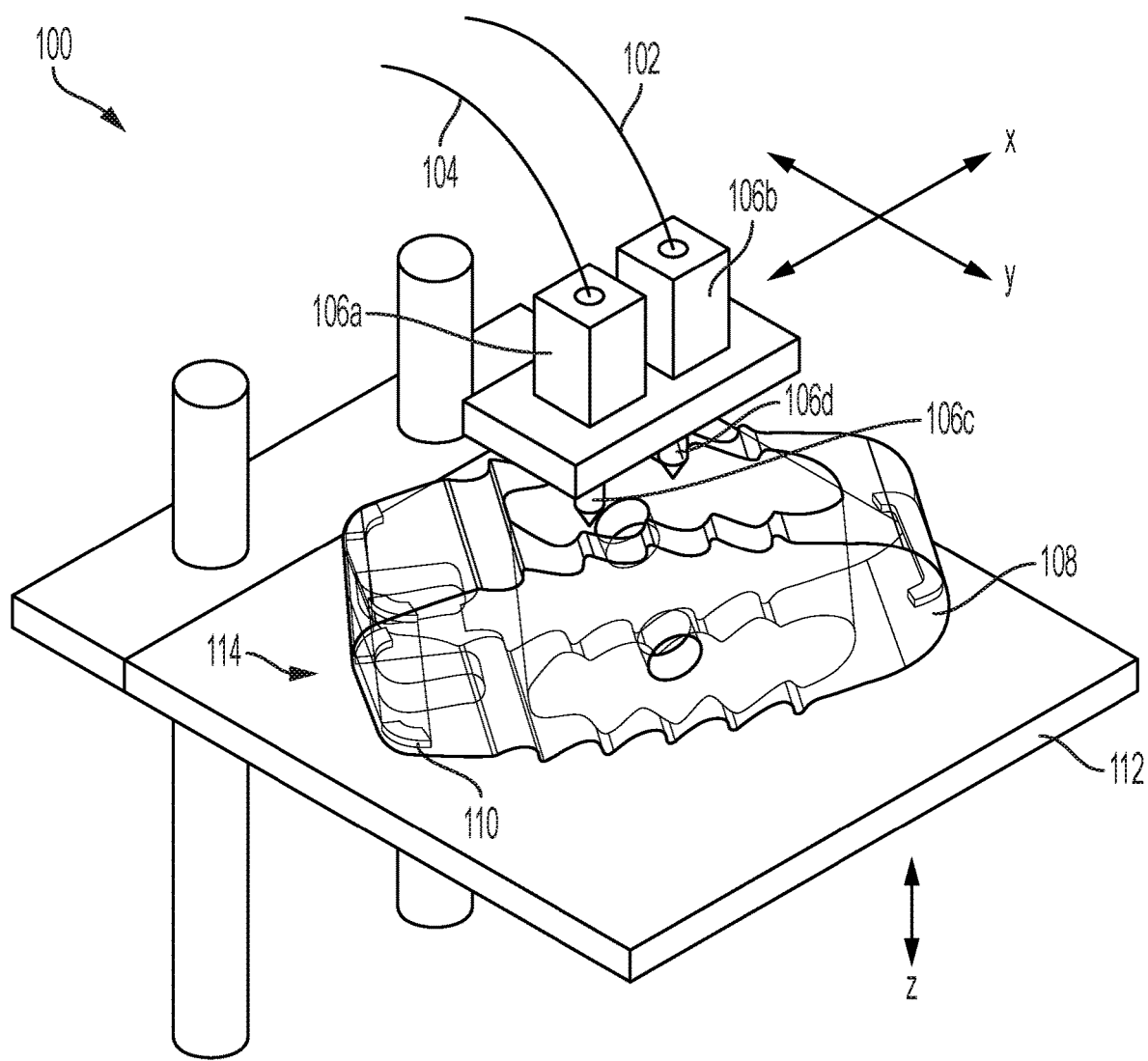
FIG. 1 illustrates an example three-dimensional printer.

The following discussion omits or only briefly describes certain conventional features related to implantable medical devices, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to implantable medical devices, and more particularly, to radio-opaque markers positioned within an implantable medical device (hereinafter "implant"). Embodiments of the present disclosure are described below with reference to the figures. It is noted that the embodiments described herein are described with respect to medical implant devices, such as intervertebral fusion implant devices. However, it is noted that the embodiments are not limited to merely intervertebral fusion implant devices or medical implant devices, rather the embodiments may be utilized in medical instruments, such as catheters, distractors, bone screws or other technologies.

FIG. 1 illustrates an example three-dimensional (3D) printer 100. In one or more cases, the 3D printer 100 may utilize fused deposition modeling (FDM), which may also be known as fused filament fabrication (FFF) or filament freeform fabrication. In one or more other cases, the 3D printer 100 may utilize a material jetting printing process, a stereolithography process, a digital light processing process, or the like.

In one or more cases, the 3D printer 100 may include one or more extrusion heads, such as extrusion head 106a and extrusion head 106b. Each extrusion head may receive its own filament, such as a filament of thermoplastic material, photopolymer material, or the like. For example, the extrusion head 106a may be configured to receive filament 104, and the extrusion head 106b may be configured to receive filament 102. In one or more cases, the filament 102 is a thermoplastic material, photopolymer material, or the like. For example, the filament 102 may be a thermoplastic material that includes a biocompatible polymer, such as PEEK, PEKK, or the like. The filament 102 may be used to create the structure of the implant 114. In one or more cases, the filament 104 includes at least a radio-opaque material. The filament 104 may be, for example, a combination of radio-opaque material with thermoplastic material or a photopolymer material. The filament 104 may be used to create markers within the implant 114 that are visible on medical imaging, such as x-rays. The filament 104, for example, may be a combination of a biocompatible polymer, such as PEEK, PEKK, or the like, and a radio-opaque material, such as barium, iodine, barium-sulfate, tantalum, titanium, or other like radio-opaque materials capable of blending with the biocompatible polymer. The combination of the thermoplastic material and the radio-opaque material may be a homogenous mixture. In yet one or more other cases, the filament 102 may be a thermoplastic polyurethane, a polylactic acid (PLA), acrylonitrile butadiene styrene (ABS), polyethylene terephthalate glycol (PETG), or the like. In one or more other cases, the filament 104 may be a combination of radio-opaque material and at least one of a thermoplastic polyurethane, a polylactic acid (PLA), acrylonitrile butadiene styrene (ABS), polyethylene terephthalate glycol (PETG), or the like. In one example, to print a medical instrument, the filament 102 may include ABS, and the filament 104 may include ABS and a radio-opaque material. In another example, to print medical tubing, the filament 102 may include PETG, and the filament 104 may include PETG and a radio-opaque material. In one or more cases, the filament 102 and the filament 104 may include the same material. For example, the filament 102 may include thermoplastic material, and, in addition to the radio-opaque material, the filament 104 may include thermoplastic material. In one or more other cases, the filament 102 and the filament 104 may include different material. For example, the filament 102 may include ABS, and, in addition to the radio-opaque material, the filament 104 may include thermoplastic material. For the cases, in which the 3D printer 100 utilizes a material jetting printing process, the filament 102 and the filament 104 may include photopolymer resin.

In one or more cases, the ratio of radiolucent thermoplastic material to radio-opaque material may vary to decrease or increase the radio-opaqueness of the one or more markers printed within the implant 114. For example, by increasing the amount of thermoplastic material and/or decreasing the amount of radio-opaque material included in the homogenous mixture of the filament 104, the radio-opaqueness of the one or more markers may decrease. Conversely, by decreasing the amount of thermoplastic material and/or increasing the amount of radio-opaque material included in the homogenous mixture of the filament 104, the radio-opaqueness of the one or more markers may increase. It should be noted that the 3D printer 100 may include more than two extrusion heads and may be configured to deposit more than two types of filaments, in which the additional filaments have varying degrees of radio-opaqueness. That is, one or more markers having more radio-opaque material may appear more visible than one or more other markers having less radio-opaque material. For example, the 3D printer 100 may include three extrusion heads that utilize three different filaments. The first extrusion head may be configured to print filament, such as filament 102, having no radio-opaque material. The second extrusion head may be configured to print filament, such as filament 104. The third extrusion head may be configured to print a third filament having a homogenous mixture of radiolucent thermoplastic material and radio-opaque material. In one or more cases, the third filament may have a homogenous mixture in which the amount of radio-opaque material is greater than the amount of radio-opaque material in the filament 102. In one or more other cases, the third filament may have a homogenous mixture in which the amount of radio-opaque material is less than the amount of radio-opaque material in the filament 102.

The 3D printer 100 may move the filament through the respective extrusion head. The extrusion heads may be configured to heat and melt the filament as the filament passes through the extrusion head and exits a nozzle, such as nozzle 106c and nozzle 106d, of the respective extrusion head. In one or more cases, the 3D printer 100 is configured to move and/or deposit one or more molten filaments under computer control to define the printed shape of the implant 114.

In one or more cases, the 3D printer 100 may be configured to move the extrusion heads to deposit one or more filaments, such as the filaments 102 and 104, in layers. The 3D printer 100 may be configured to vary the speed in which the extrusion heads start and stop depositing the respective filaments. The 3D printer 100 may be configured to deposit the one or more filaments, such that the filaments are deposited in a plane without stringing or dribbling between layers of the printed layers. One horizontal plane of one or more filaments may be deposited at a time. In one or more cases, the 3D printer 100 is configured to move the extrusion heads in x and y directions to deposit a horizontal plane of one or more molten filaments. During the initial depositing of the one or more filaments, the 3D printer 100 may deposit the one or more molten filaments, via the extrusion heads, on the build platform 112 of the 3D printer. Having finished depositing an initial layer in the horizontal plane on the build platform 112, the extrusion heads may move upwards in the z direction to begin depositing the next layer. In one or more cases, the extrusion heads may move upwards in the z direction and deposit another horizontal layer. This process repeats until the implant 114 is printed.

In one or more cases, the 3D printer 100 deposits filaments 102 and filaments 104 in the same horizontal plane, i.e., the same layer, to provide different material to different parts of the implant 114. For example, the filament 102 may be deposited in a portion 108 of the implant 114 that defines a structural portion of the implant 114, and the filament 104 may be deposited in a portion 110 of the implant 114 that defines a marker portion of the implant 114.

In one or more other cases, the 3D printer 100 may deposit the filament 102 in multiple layers and to leave one or more voids within the multiple layers of filament 102. The void may be formed in the shape of the respective marker, thereby serving as a mold and/or compartment for the filament 104 to be inserted therein. The 3D printer 100 may deposit the filament 104 within the one or more voids. The 3D printer 100 may deposit the filament 102 over the filament 104. In one or more cases, the 3D printer 100 may partially deposit the filament 102 over the filament 104, such that a portion of the filament 104 within a void is covered by the filament 102. In one or more other cases, the 3D printer 100 may deposit the filament 102 over the filament 104, such that the filament 104 within a void is completely covered by the filament 102.

The implant 114, described herein to exemplify the one or more embodiments of the present disclosure, is an intervertebral fusion device. The implant 114 may include one or more features of the implant devices described in U.S. Patent Application Publication Number 2008/0161927, which is incorporated herein by reference in its entirety. Moreover, the implant 114 may include one or more features of the implant devices and may be utilized with one or more instruments, such as those described in U.S. Pat. No. 7,476,252 (hereinafter the "'252 patent"), which is incorporated herein by reference in its entirety.

The implant 114 includes an upper wall 32 and a lower wall 34. Side wall 36 and side wall 38 extend in a generally orthogonal direction from the upper wall 32 and the lower wall 34. Side wall 40 and sidewall 42 extend generally orthogonally from the side wall 36 and the sidewall 38. In one or more cases, the upper wall 32 and the lower wall 34 are generally parallel to one another; the side wall 36 and the sidewall 38 are generally parallel to one another; and the side wall 40 and the sidewall 42 are generally parallel to one another. In one or more cases, one or more projections 52 may extend from the upper wall 32 and the lower wall 34, respectively. The projections 52 may be integrally formed with and project from the upper wall 32 and the lower wall 34. One or more cases, the projections 52 are generally triangular as viewed from a side profile and extend across the upper wall 32 and the lower wall 34. In one or more other cases, the projections may take other suitable shapes including keels, pyramids, cones, and spikes.

Figure 2A:
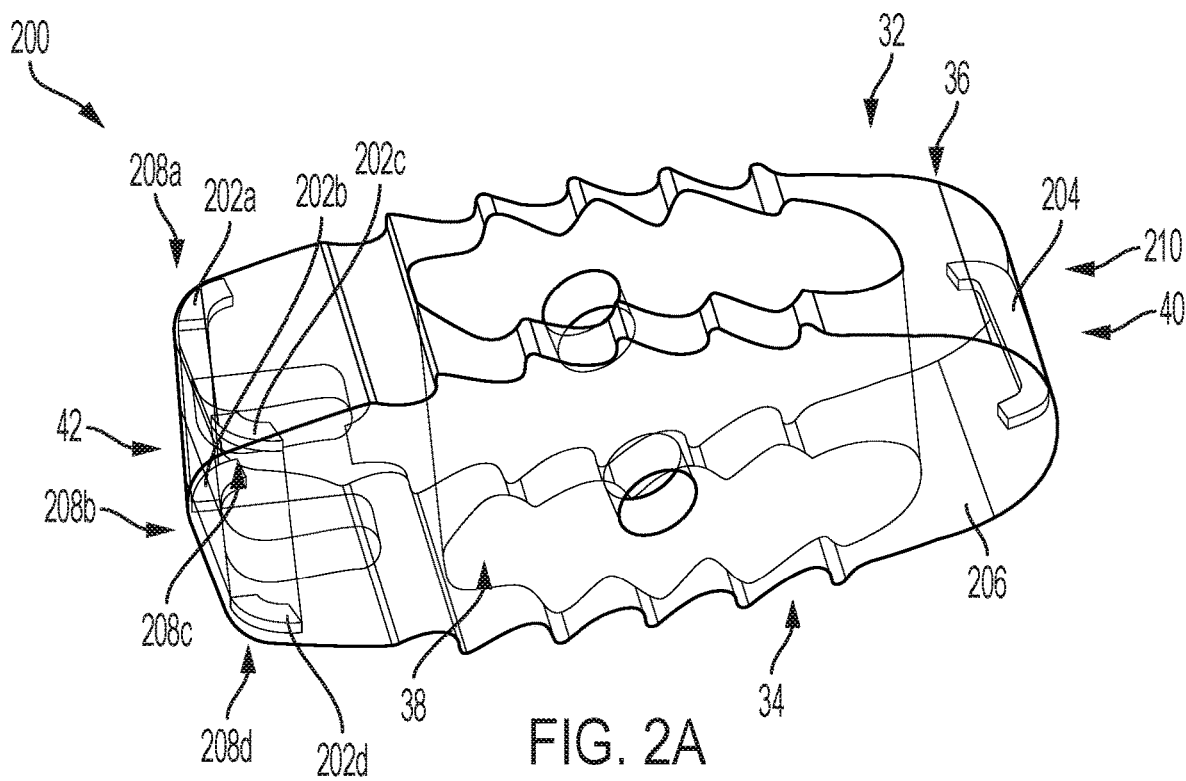
FIG. 2A illustrates a perspective view of one or more example markers indicating one or more edges of an example implant.
Figure 2B:
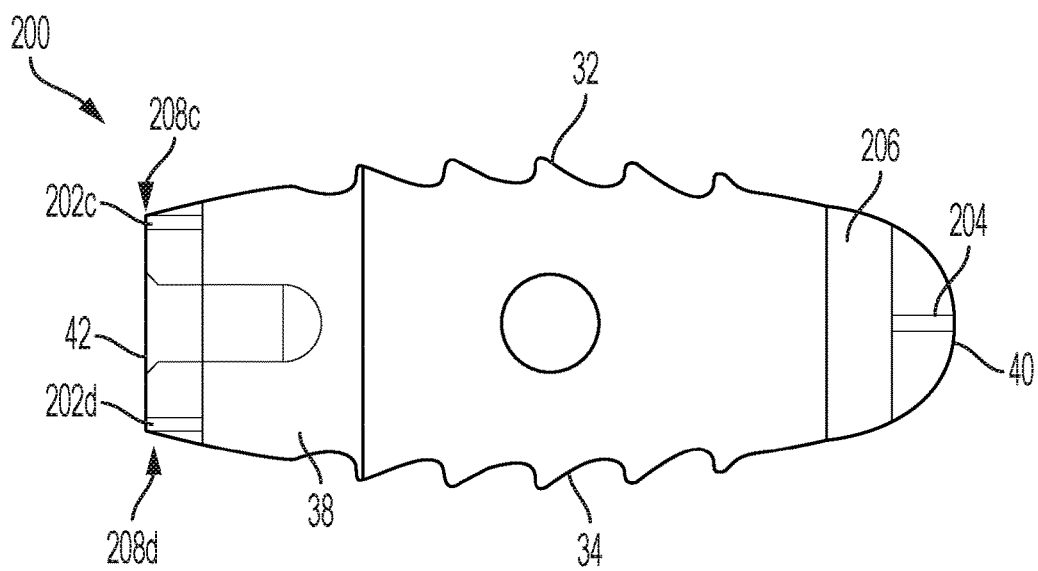
FIG. 2B illustrates a side view of the one or more example markers of FIG. 2A.

FIG. 2A illustrates a perspective view of one or more example markers, such as markers 202a, 202b, 202c, 202d, and 204, indicating one or more edges, such as edges 208a, 208b, 208c, and 208d of an example implant 200. FIG. 2B illustrates a side view of the one or more example markers 202a, 202b, 202c, 202d, and 204 of FIG. 2A.

In one or more cases, the 3D printer 100 may print the implant 200 such that one or more markers distinguish the edges of the implant 200. For example, one or more markers, such as markers 202a, 202b, 202c, and 202d, may be printed on edges 208a, 208b, 208c, and 208d, respectively. Edge 208a may define an upper corner area where the side wall 42, the sidewall 36, and the upper wall 32 converge. The marker 202a may define such corner area of edge 208a. Edge 208c may define an upper corner area where the side wall 42, the sidewall 38, and the upper wall 32 converge. The marker 202c may define such corner area of edge 208c. Edge 208b may define a lower corner area where the side wall 42, the sidewall 36, and the lower wall 34 converge. The marker 202b may define such corner area of edge 208b. Edge 208d may define a lower corner area where the side wall 42, the sidewall 38, and the lower wall 34 converge. The marker 202d may define such corner area of edge 208d.

In another example, a marker, such as marker 204, may be printed on an edge, such as edge 210, which includes parallel walls, such as sidewall 36 and sidewall 38. For example, edge 210 may define an area where the sidewall 36, the sidewall 38, and the sidewall 40 converge. The marker 204 may define the area of edge 210. By printing markers to distinguish one or more edges of the implant, or other locations of the implant, a user may be able to visualize the edges or other locations of the implant 200 in order to position the implant 200 between endplates of adjacent vertebrae in various orientations and confirm not only the orientations but the relative locations of various portions of the implant. Moreover, by printing markers to distinguish one or more edges of the implant, or other locations of the implant, a user may be able to determine whether the implant 200 subsided into a vertebral endplate post-implantation.

In one or more cases, the markers, such as markers 202a, 202b, 202c, and 202d, may be printed in a manner congruent with a shape of the respective edges, edge 208a, 208b, 208c, and 208d. For example, for the cases in which the edge 208a is curved, the marker 202a may be curved to be consistent with the curvature of the edge 208a. In another example, for the cases in which the edge 208a includes right angles, the marker 202a may be printed to be consistent with the right angles of the edge 208a. In one or more cases, the markers may be exposed to the outer surface of the implant 200. For example, a portion of the marker 202a may be exposed on the outer surfaces of the side wall 42, the sidewall 36, and the upper wall 32. In one or more other cases, the markers may be embedded with the implant 200 such that material deposited from filament 102 covers the marker from the outer surface of the implant 200.

In one or more cases, the marker 204 may be printed in a manner congruent with a shape of edge 210. For example, for the cases in which the edge 210 is curved, the marker 204 may be curved to be consistent with the curvature of the edge 210. In another example, for the cases in which the edge 210 includes right angles, the marker 204 may be printed to be consistent with the right angles of the edge 210. In one or more cases, the marker 204 may be positioned in a middle area of the sidewall 36, the sidewall 38, and the sidewall 40.

Figure 3:
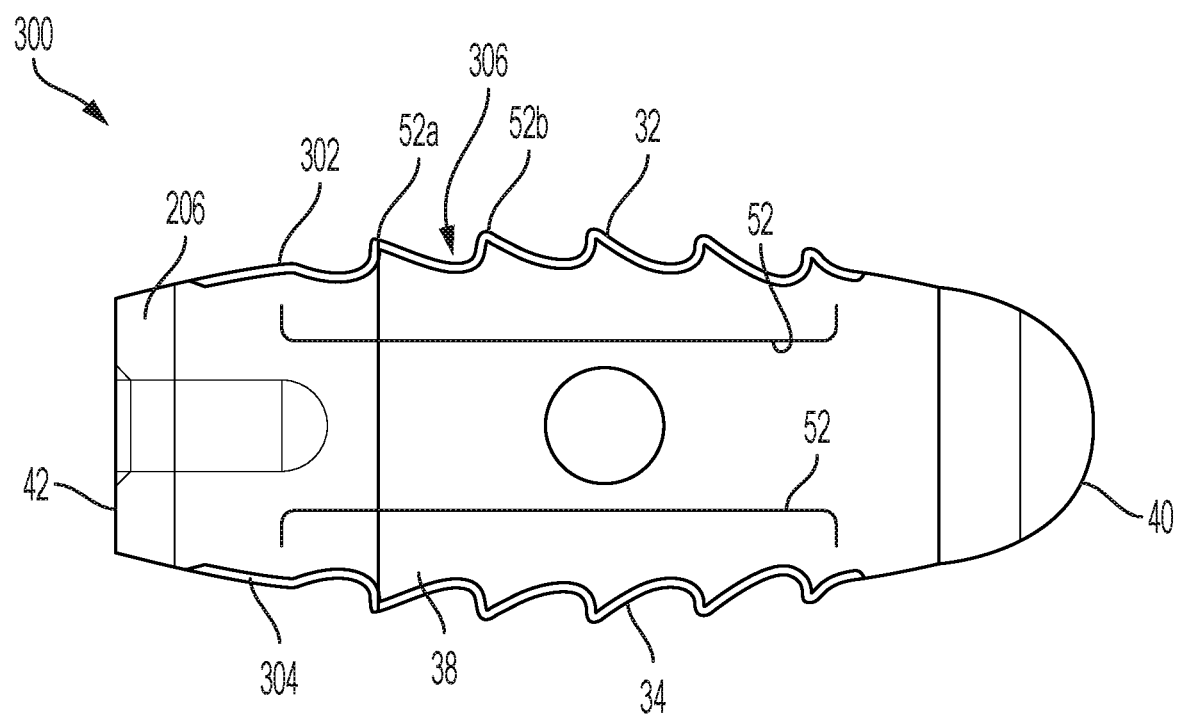
FIG. 3 illustrates a side view of one or more example markers indicating one or more sides of an example implant.

FIG. 3 illustrates a side view of one or more example markers, such as marker 302 and marker 304, indicating one or more sides, such as upper wall 32 and lower wall 34, of an example implant 300.

In one or more cases, the 3D printer 100 may print the implant 300 such that one or more markers distinguish one or more sides of the implant 300. For example, marker 302 may be printed on the upper wall 32. In another example the marker 304 may be printed on the lower wall 34. In yet another example, the markers 302 and 304 may be printed on the upper wall 32 and the lower wall 34, respectively. In one or more cases, the marker may be printed on an entire surface of the side of the implant 300. In one or more other cases, the marker may be printed on a portion of the surface of the side of the implant. In yet one or more other cases, the marker may be printed in selected areas of the side of the implant. For example, the marker may be printed in one or more recessed areas, such as recessed area 306, between two projections, such as projection 52a and 52b. By printing markers to distinguish one or more sides of the implant, a user may be able to visualize the sides of the implant 300 in order to position the implant 300 between endplates of adjacent vertebrae.

Figure 4A:
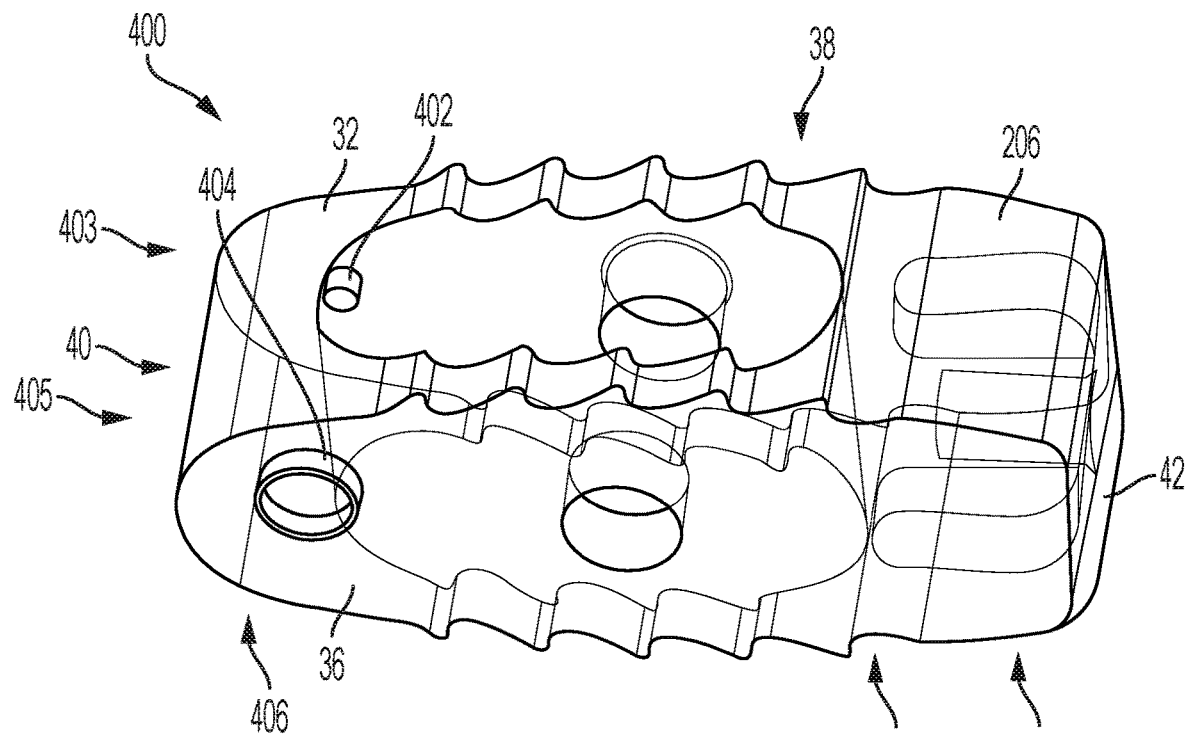
FIG. 4A illustrates a perspective view of example markers indicating an orientation of an example implant.
Figure 4B:
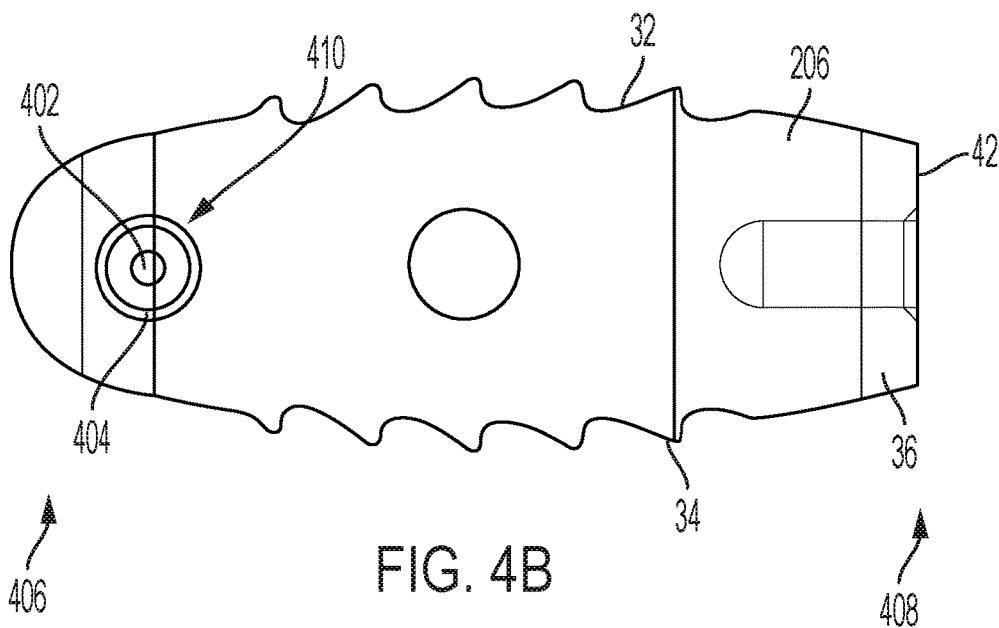
FIG. 4B illustrates a side view of the one or more example markers of FIG. 4A.
Figure 4C:
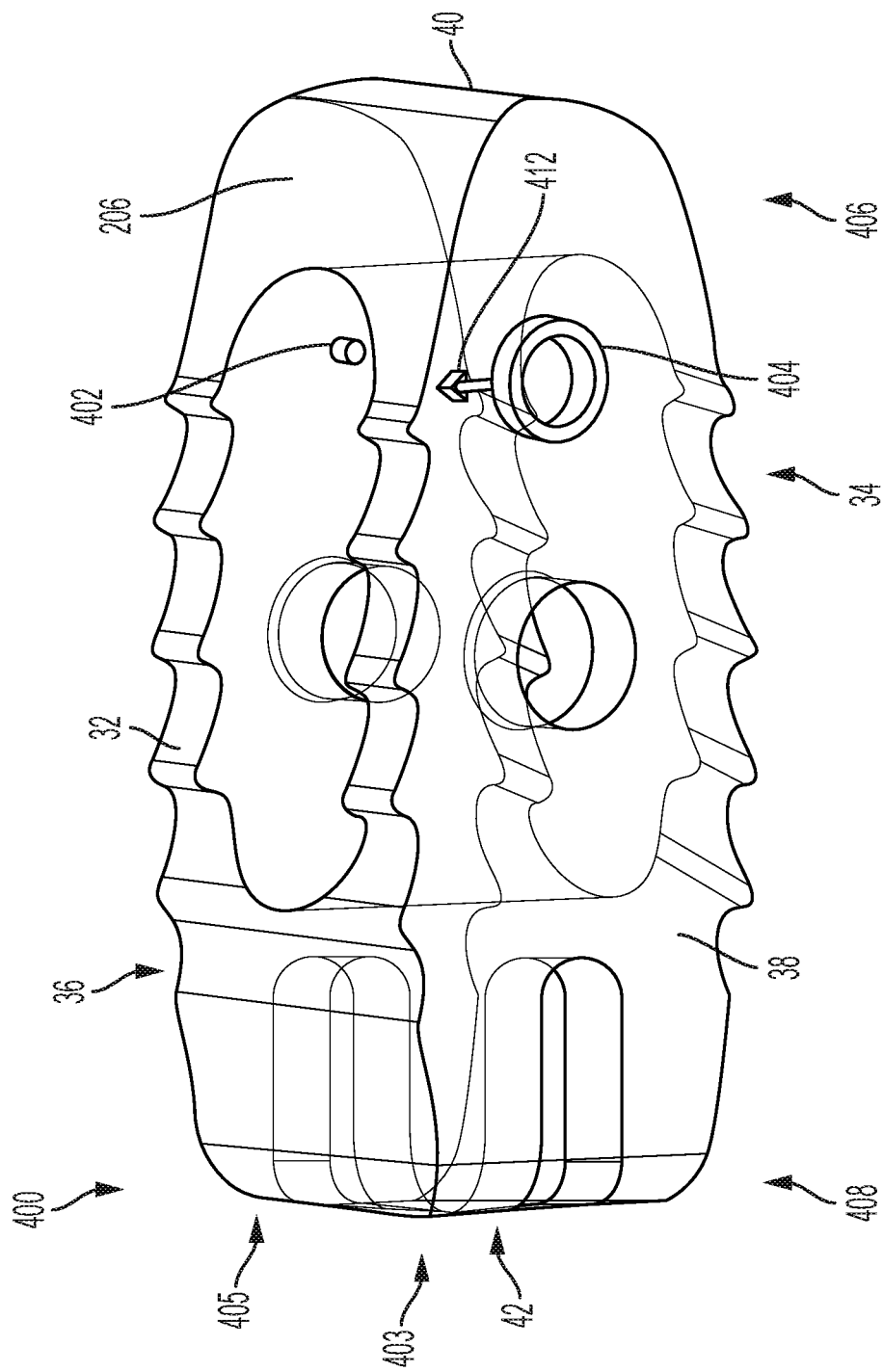
FIG. 4C illustrates a perspective view of an example indicator marker indicating a position of the one or more example markers of FIGS. 4A and 4B.

FIG. 4A illustrates a perspective view of example markers 402 and 404 indicating an orientation of an example implant 400. FIG. 4B illustrates a side view of the one or more example markers 402 and 404 of FIG. 4A. FIG. 4C illustrates a perspective view of an example indicator marker 412 indicating a position of the one or more example markers 402 and 404 of FIGS. 4A and 4B.

In one or more cases, the 3D printer 100 may print the implant 400, such that one or more markers may be used to determine an orientation of the implant 400. Markers, such as markers 402 and 404, may be printed within two areas of the structure of the implant 400, and by viewing the implant 400 from a certain perspective, a user may determine the orientation of the implant 400. For example, markers 402 and 404 may each be printed in an anterior area 406 of the implant 400, in which marker 402 is printed within one side portion 403 of the implant 400 and marker 405 is printed within an opposite side portion 405 of the implant 400. It is noted that the markers 402 and 404 may be printed on the posterior area 408 of the implant 400. It is also noted that the marker 402 may be printed within one side portion 405 of the implant 400 and the marker 405 may be printed within an opposite side portion 403 of the implant 400.

The markers may be formed in a variety of shapes which may indicate an orientation of the implant 400. For example, the marker 402 may be printed in a cylindrical shape having a solid center, and marker 404 may be printed in a cylindrical shape that is larger than the size of the marker 402 and has a hollow center. When viewed from a side perspective view, such as by viewing the markers 402 and 404 through the side wall 36, the marker 402 may appear as a dot and the marker 404 may appear as a ring. Via the side perspective view, a user may align the implant 400 between two endplates of the vertebrae by orienting the marker 402 to be within the center of the marker 404. A user may also determine the orientation of the implant 400 post-operation by determining whether the marker 402 is centrally aligned 410 with the marker 404.

In one or more other cases, an example indicator marker 412, as shown in FIG. 4C, may be printed within the implant 400 to indicate the orientation of the surfaces of the implant 400. The indicator marker may be printed in various shapes, in which the shape has a characteristic on one end of the shape that defines a position on the implant 400. For example, the indicator marker 412 may be printed in an arrow shape, in which the point of the arrow is the characteristic of the indicator marker 412 to determine a position of the markers 402 and 404. The indicator marker 412 may be positioned on either side portion 403 or side portion 405. The indicator marker 412 may be printed in an anterior area 406 or a posterior area 408 of the implant 400. The indicator marker 412 may be used to indicate the position of the markers 402 and 404 with respect to the side portion 403 and the side portion 405. For example, for the cases in which the indicator marker 412 is positioned on the side portion 403 and adjacent to the marker 404, if a user determines that the arrow of the indicator marker 412 is pointed upwards, then the user knows the marker 404 is in front of the marker 402, based on the side perspective view of the user viewing the image of the implant 400. For the cases in which the indicator marker 412 is positioned on the side portion 403 and adjacent to the marker 404, if a user determines that the arrow of the indicator marker 412 is pointed downwards, then the user knows the marker 404 is behind the marker 402, based on the side perspective view of the user viewing the image of the implant 400.

Figure 5A:
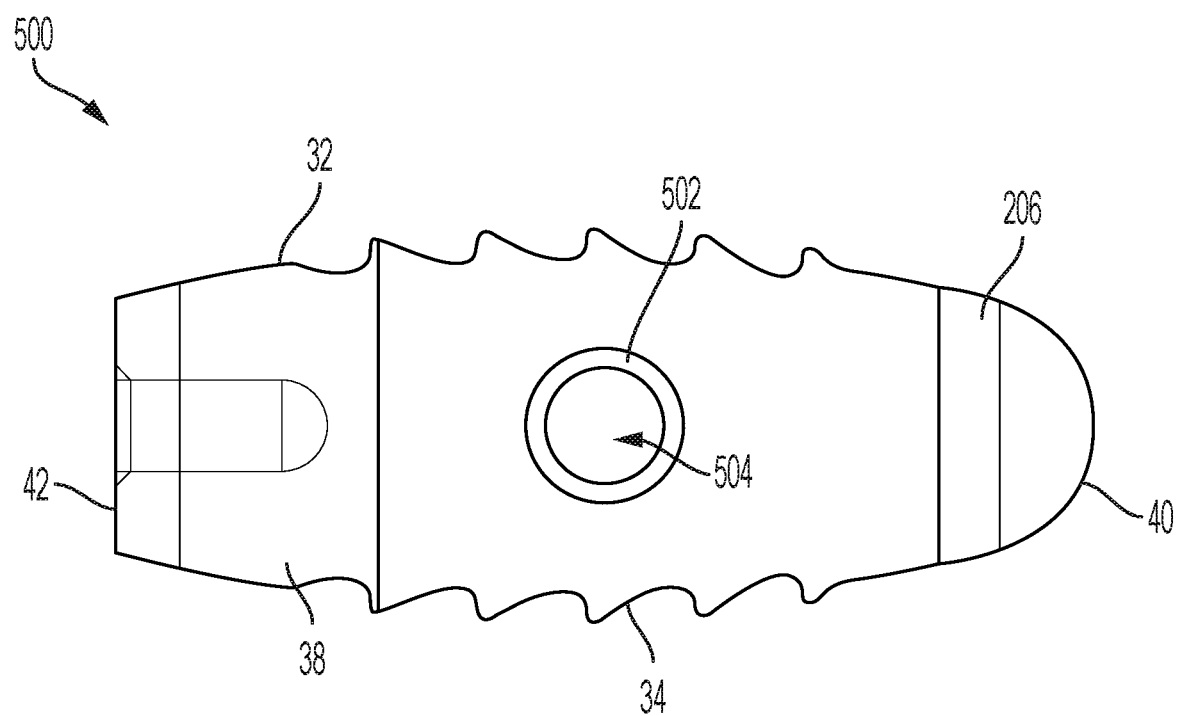
FIG. 5A illustrates a side view of an example marker indicating an orientation and/or feature of an example implant.
Figure 5B:
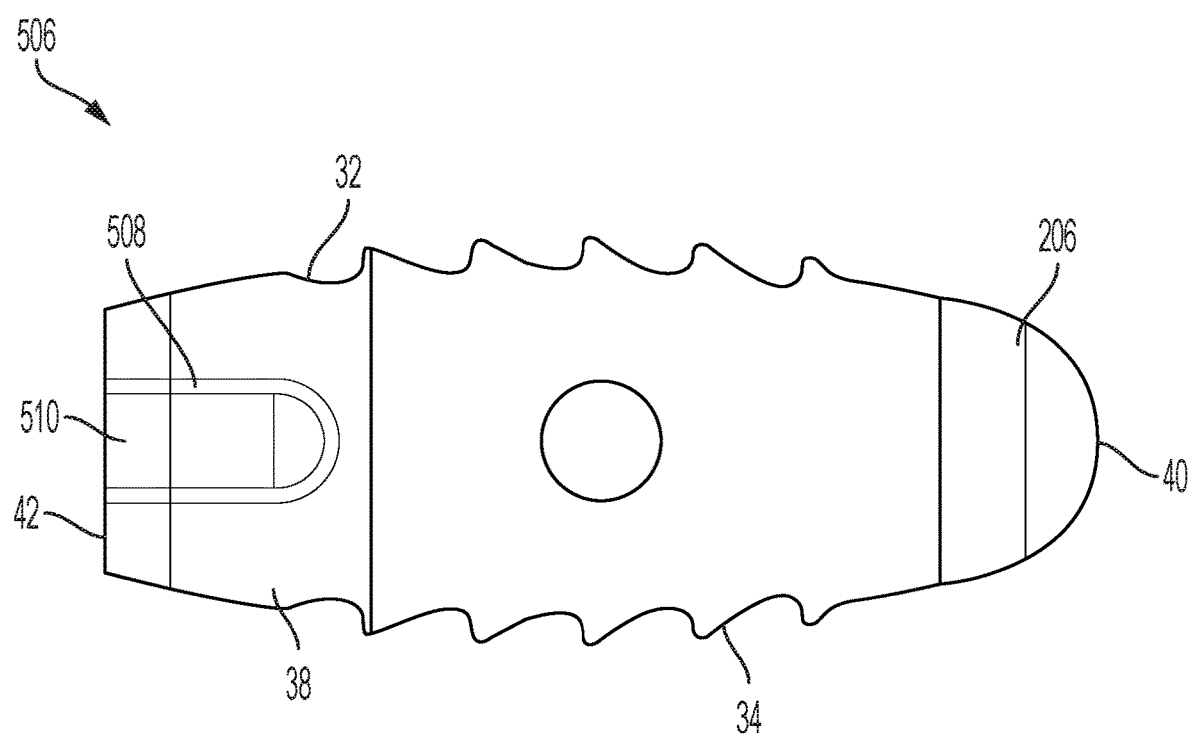
FIG. 5B illustrates a side view of an example marker indicating a feature of an example implant.

FIG. 5A illustrates a side view of an example marker 502 indicating an orientation and/or feature of an example implant 500. FIG. 5B illustrates a side view of an example marker 508 indicating a feature of an example implant 506. In one or more cases, the 3D printer 100 may print one or more markers within an implant to define one or more features of the implant that may be accessed during an operation via medical images, such as x-ray images.

For example, a marker 502 may be printed within a side portion and/or on a side wall, such as sidewall 38, of the implant 500. The marker 502 may also be printed to align with an opening 504 of the implant 500. In one or more cases, the marker 502 may be printed in a shape that corresponds with the shape of the opening 504. For example, the marker 502 may be printed in a cylindrical shape or a circular shape for the cases in which the opening has a circular shape when viewed from a side perspective view. In one or more cases, the implant 500 may be aligned when the marker 502 is aligned with the opening 504 of the implant 500. For example, the implant 500 may be aligned between two endplates when the circular marker 502 overlaps the circular opening 504.

In another example, the marker 502 may be printed on a sidewall, such as sidewall 38, to encompass the diameter the hole 504. By encompassing the diameter of the hole 504, the marker 502 may improve the visibility of the hole 504. The improved visibility of the hole 504 may aide a user in injecting a therapy into the implant 500 via the hole 504. In yet another example, the marker 508, as shown in FIG. 5B, may be printed to define a slot 510 for an inserter attachment and/or extractor attachment. The inserter and extractor attachments are further described in the '252 patent. Accordingly, a description of such features is not repeated.

Figure 6:
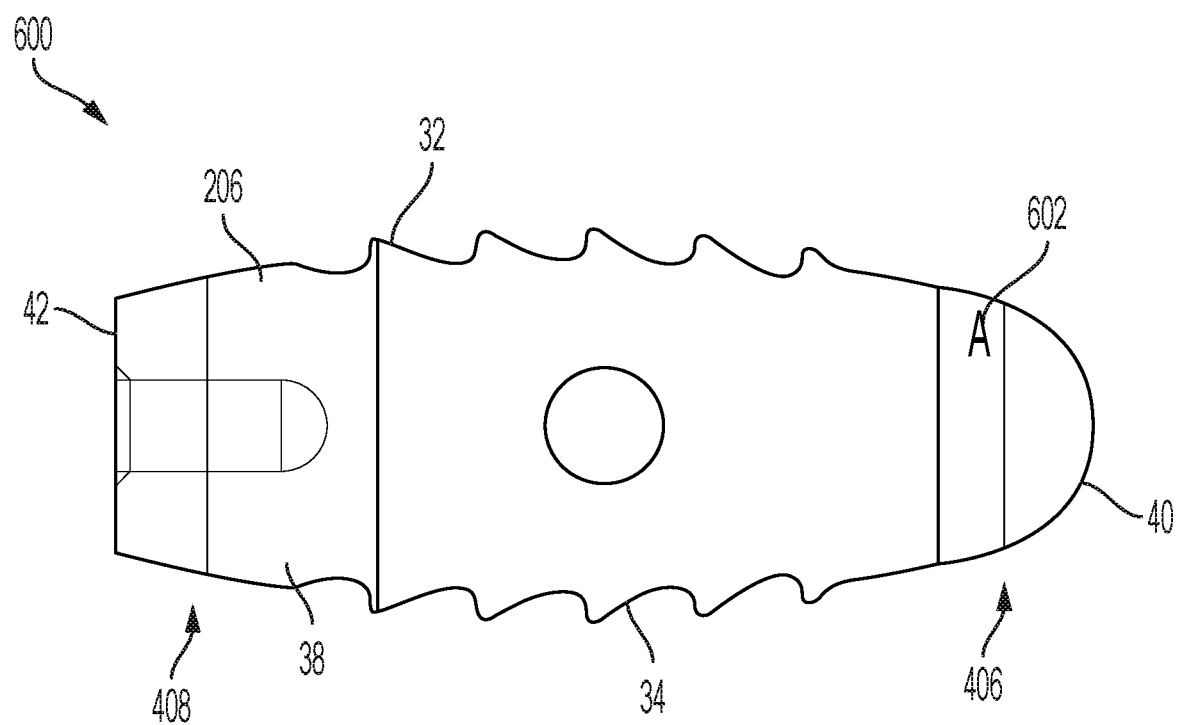
FIG. 6 illustrates a side view of an example marker indicating an orientation of an example implant.

FIG. 6 illustrates a side view of an example marker 602 indicating an orientation of an example implant 600. In one or more cases, the 3D printer 100 may print one or more markers that indicate how the implant 600 is inserted, for example, between two endplates. For example, the marker 602 may be printed with an "A", "anterior", or other like variations in the anterior area 406 of the implant 600, in which the marker 602 indicates that anterior area 406 of the implant 600. In another example, the marker 602 may be printed with a "P", "posterior", or other like variations in the posterior area 408 of the implant 600, in which the marker 602 indicates that posterior area 408 of the implant 600. In yet other examples to indicate both the anterior and posterior areas of the implant 408, a marker may be printed with an "A" in the anterior area 406, and another marker may be printed with a "P" in the posterior area 408.

Figure 7:
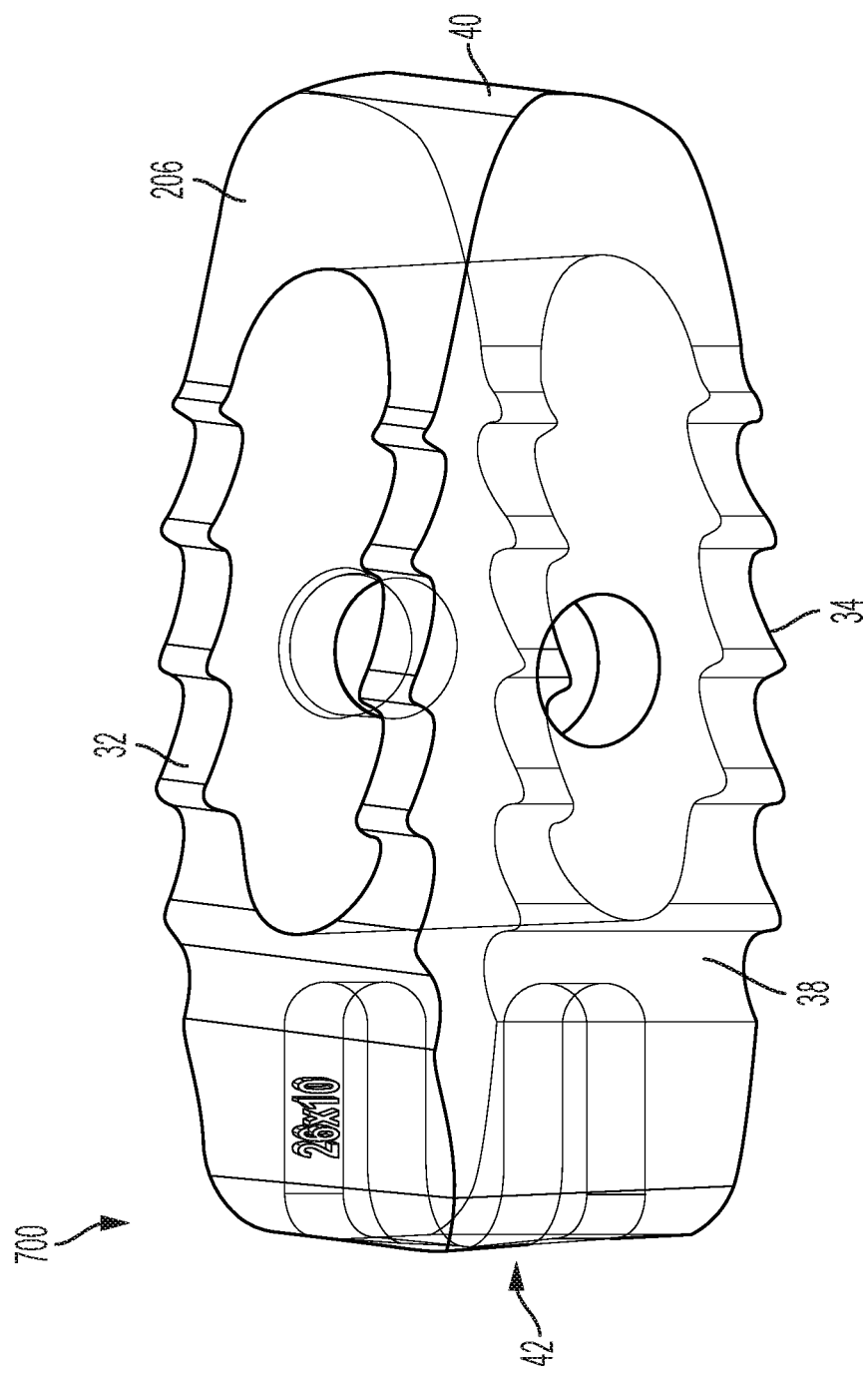
FIG. 7 illustrates a perspective view of an example marker indicating a feature of an example implant.

FIG. 7 illustrates a perspective view of an example marker 702 indicating a feature of an example implant 700. In one or more cases, the 3D printer 100 may print one or more markers, such as marker 702, within the implant 700 to define one or more features of the implant 700. For example, the marker 702 may be printed to indicate a size (e.g., 26 mm×10 mm) of the implant 700. In another example, the marker 702 may be printed to indicate a part number of the implant 700, a lot number (e.g., Lot12345) of the implant 700, a serial number of the implant 700, and/or other like identifiers such as numbers, characters, phrases, or codes. In yet another example, the marker 702 may be printed to indicate a company name (e.g., Medtronic) or logo.

Figure 8:
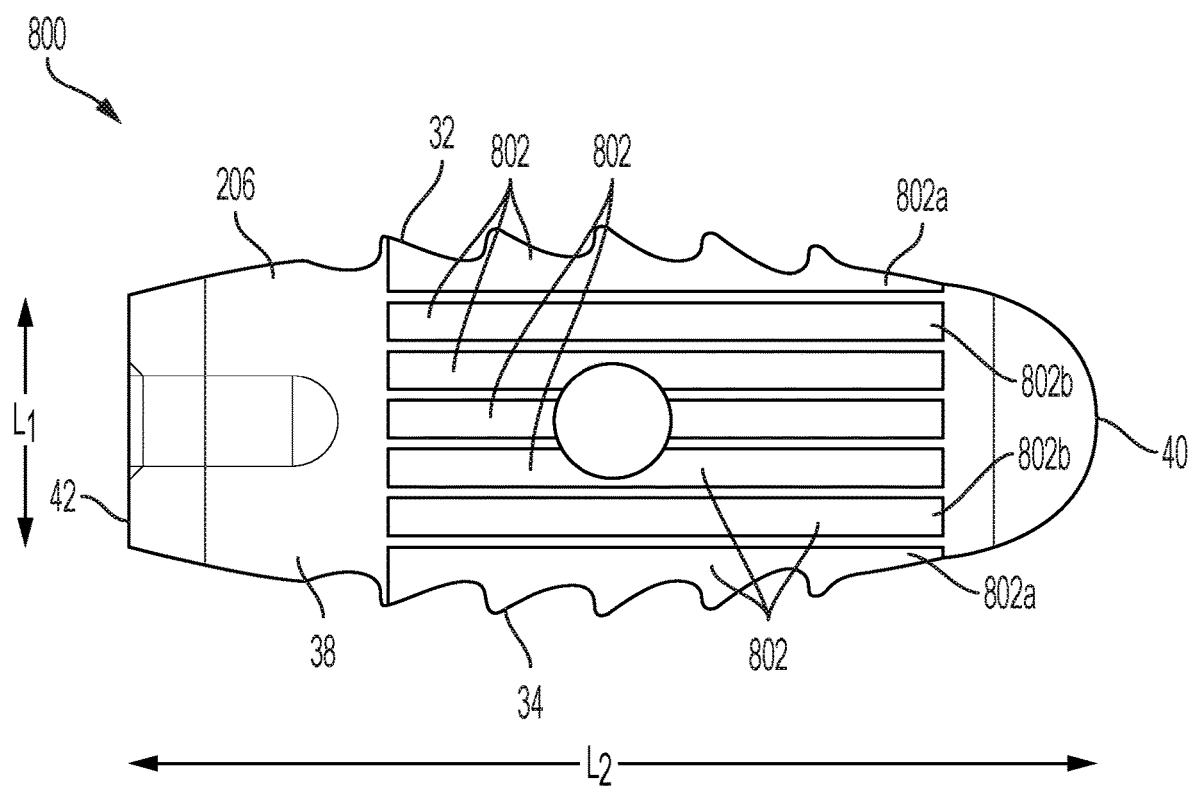
FIG. 8 illustrates a side view of one or more example markers indicating a progress of bone fusion through an example implant.

FIG. 8 illustrates a side view of one or more example markers 802 indicating a progress of bone fusion through an example implant 800. In one or more cases, the 3D printer 100 may print one or more markers 802 that may be used as a gauge to measure the progress of bone fusion through the implant 800. The one or more markers 802 may be printed within a side portion and/or on a side wall, such as sidewall 38, of the implant 800.

In one or more cases, the markers 802 may be arranged in series and extend in one or more directions, for example a longitudinal direction $L_1$ and/or a lateral direction $L_2$, across the implant 800. For example, the markers 802 may extend across the implant 800 in the lateral direction $L_2$ of the implant 800, and may be serially arranged in the longitudinal direction $L_1$ of the implant 800. In another example, the markers 802 may extend across the implant 800 in the longitudinal direction $L_1$ of the implant 800, and may be serially arranged lateral direction $L_2$ of the implant 800. In yet another example, a first set of markers 802 may extend across the implant 800 in the lateral direction $L_2$ of the implant 800 and may be serially arranged in the longitudinal direction $L_1$ of the implant 800, and a second set of markers may extend across the implant 800 in the longitudinal direction $L_1$ of the implant 800 and may be serially arranged lateral direction $L_2$ of the implant 800.

When viewed on a medical image, one or more of the markers 802 may be faded or not visible as the bone fusion progresses through the implant 800. For example, a medical image of the implant 800 may be take one month after an operation, in which the outer markers 802*a* are faded. Another image of the implant 800 may be taken at a subsequent time, in which the outer markers 802*a* are no longer visible and the next set of markers 802*b* are faded, thereby indicating that the bone fusion progressed the distance between marker 802*a* and 802*b* through the implant 800.

It is noted that in one or more cases the features described above with respect to implants 114, 200, 300, 400, 500, 506, 600, 700, and 800 may be implemented in only the respective implants, and in one or more other cases such features from two or more implants may be combined in one implant. For example, the features describe in implant 400 may be combined with the features of implant 506 and implant 700. It is also noted that the markers described herein may be printed to have various thicknesses and/or sizes based on the size of the respective implant.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A three-dimensional (3D) printing method for forming an implantable medical device, the method comprising:
   printing a structure of the implantable medical device by depositing a first thermoplastic material, the first thermoplastic material being radiolucent; and
   printing one or more radio-opaque markers by depositing another material comprising at least a radio-opaque material, the one or more radio-opaque markers indicating a relative orientation of the implantable medical device with respect to human anatomy when the implantable medical device is implanted within a human body;
   wherein the one or more radio-opaque markers are integrated with the structure of the 3D object;
   wherein the printing the one or more radio-opaque markers comprises:
      printing a first radio-opaque marker within a first area of the structure of the implantable medical device, the first radio-opaque marker comprising an annular shape having an outer diameter and an inner diameter;
      printing a second radio-opaque marker within a second area of the structure of the implantable medical device, the second radio-opaque marker having an outer perimeter;
   wherein the relative orientation of the implantable medical device may be determined to be properly oriented by viewing the implantable medical device from a side perspective view X-ray and the perimeter of the second radio-opaque marker is visible within an area defined by the inner diameter of the first radio-opaque marker.

2. The method of claim 1, wherein the one or more radio-opaque markers comprises at least a first radio-opaque marker and a second radio-opaque marker that are visible on an x-ray image of the implantable medical device for cooperatively indicating a relative orientation of the implantable medical device.

3. The method of claim 1, wherein the first thermoplastic material comprises a biocompatible polymer.

4. The method of claim 1, wherein the radio-opaque material comprises at least one of barium, iodine, barium-sulfate, tantalum, and titanium.

5. The method of claim 1, wherein the printing the one or more radio-opaque markers comprises printing the one or more radio-opaque markers on one or more edges of the structure of the implantable medical device.

6. The method of claim 5, wherein the printing the one or more radio-opaque markers comprises printing the one or more radio-opaque markers in a shape congruent with the shape of the one or more edges of the implantable medical device.

7. The method of claim 1, wherein the printing the one or more radio-opaque markers comprises printing the one or more radio-opaque markers on one or more sides of the implantable medical device.

8. The method of claim 1, further comprising:
   aligning the implantable medical device such that the perimeter of the second radio-opaque marker is completely visible within an area defined by the inner diameter of the first radio-opaque marker.

9. The method of claim 1, further comprising:
   positioning the implantable medical device between a superior vertebrae and an inferior vertebrae of a human spine such that, when taking a side view X-ray, the first radio-opaque marker is coaxially aligned with the second radio-opaque marker.

10. The method of claim 1, wherein the printing the one or more radio-opaque markers comprises:
    printing a third radio-opaque marker within a third area of the structure of the implantable medical device, the third radio-opaque marker having an arrow shape including a point,
    wherein the third area is located on a same side of the implantable medical device as the first area, and a position of the first radio-opaque marker is determined based on an orientation of the point of the arrow shape of the third radio-opaque marker.

11. The method of claim 1, wherein the printing the one or more radio-opaque markers comprises printing at least one of the one or more radio-opaque markers around at least one opening in the structure of the implantable medical device.

12. The method of claim 11, wherein the at least one opening is configured to receive a surgical instrument, and the radio-opaque marker defines a size and shape of the opening, under x-ray images, for cooperative use when inserting the surgical instrument into the at least one opening.

13. The method of claim 1, wherein the printing the one or more radio-opaque markers comprises printing the one or more radio-opaque markers to indicate at least one of, a size of the implantable medical device, a part number of the implantable medical device, a lot number of the implantable medical device, a serial number of the implantable medical device, and a company name of the implantable medical device.

14. The method of claim 1, wherein the printing the one or more radio-opaque markers further comprises printing a sequential series of radio-opaque bone fusion markers within the structure of the implantable medical device,
wherein each radio-opaque bone fusion marker extends for a length in a first direction of the implantable medical device, and
wherein the series of radio-opaque markers are sequentially stacked in a second direction of the implantable medical device that is opposite the first direction.

15. The method of claim 14, wherein the series of radio-opaque markers forms a gauge to measure a progress of bone fusion through the implantable medical device.

16. The method of claim 1, wherein the another material is a homogenous mixture of a second thermoplastic material and the radio-opaque material.

17. A three-dimensional (3D) printing method for forming an implantable medical device, the method comprising:
printing a structure of the implantable medical device by depositing a first thermoplastic material, the first thermoplastic material being radiolucent; and
printing one or more radio-opaque markers by depositing a radio-opaque material, the one or more radio-opaque markers being configured to indicate a relative orientation and relative position of the implantable medical device when the implantable medical device is implanted within a human body,
wherein the one or more radio-opaque markers are integrated with the structure of the implantable medical device,
wherein the printing the one or more radio-opaque markers step further comprises:
printing a first radio-opaque marker having an annular shape within a first area of the structure of the implantable medical device; and
printing a second radio-opaque marker having a circular shape within a second area of the structure of the implantable medical device, and
wherein the implantable medical device is oriented by aligning the first radio-opaque marker and the second radio-opaque marker such that, in an X-ray image, the second radio-opaque marker is visible within and aligned relative to an interior diameter of the first radio-opaque marker.

18. The method of claim 17, wherein the first thermoplastic material comprises a biocompatible polymer, and
wherein the radio-opaque material comprises at least one of barium, iodine, barium-sulfate, tantalum, and titanium.

19. The method of claim 17, wherein the printing one or more radio-opaque markers step further comprises printing a homogenous mixture of a second thermoplastic material and the radio-opaque material.

20. The method of claim 17, wherein the printing the one or more radio-opaque markers comprises printing the one or more radio-opaque markers to indicate at least one of, a size of the implantable medical device, a part number of the implantable medical device, a lot number of the implantable medical device, a serial number of the implantable medical device, and a company name of the implantable medical device.

* * * * *